United States Patent [19]

Szekely

[11] 4,003,706
[45] Jan. 18, 1977

[54] METHOD AND REAGENTS FOR THE DETECTION, ESTIMATION AND QUANTITATIVE DETERMINATION OF NITRATE IONS

[75] Inventor: Eugen Szekely, Beer-Sheva, Israel

[73] Assignee: Ben-Gurion University of the Negev Research & Development Authority, Beer-Sheva, Israel

[22] Filed: Jan. 21, 1976

[21] Appl. No.: 650,851

[30] Foreign Application Priority Data

Feb. 21, 1975 Israel .................................. 46677

[52] U.S. Cl. .............................. 23/230 R; 252/408
[51] Int. Cl.$^2$ ...................................... G01N 31/22
[58] Field of Search ................... 23/230 R; 252/408

[56] References Cited

OTHER PUBLICATIONS

Szekely, E., Talanta 14, 944 (1967).
Garcia et al., Anal. Chem. 14, 96 (1942).
Wolf, B., Anal. Chem. 15, 248 (1943).
Caldwell et al., Anal. Abstr. 6, 514 (1959).

*Primary Examiner*—Robert M. Reese

[57] ABSTRACT

Reagent and method for the detection, estimation and quantitative determination of nitrate ions by mixing the reagents with aqueous nitrate samples, the intensity of the color reactions which result being proportional to the nitrate content of the samples which can be precisely measured by photometric measurements or estimated by comparison with color standards.

24 Claims, No Drawings

Thus, for the first time it is possible to have very sensitive stable reagents, specific for nitrate ions, which react quickly and develop sufficient stable colors, suitable for precise quantitative determinations and also for rapid estimations in routine field work. The components of (a) are the chromogen in the reagents (blue colors when diphenylamine are used, λ max at 600 nm, or violet colors with their sulfonic acids, λ max at 570 nm) but the specificity, color stability and speed of the reactions are due to the other components. Precise quantitative determinations can be made only when components (b), (c), (d), (e) are also present in the reagents. High stability of the reagents is achieved only with the above given special combination of the components.

The new reagents are specific to the nitrate ions, and the influence of various ions on the test is extremely slight. The detection and visual estimation are not disturbed at all even by considerable amount of oxidizing agents, such as persulfate, chromate, chlorine, nitrites, etc. reducing agents such as sulfite, etc. In quantitative determination the presence of up to 10 ppm chlorine, up to 10 ppm chromate, up to 100 ppm persulfate, or up to 100 ppm sulfite have no influence on the precision. Inorganic acids and organic acids, such as formic, oxalic, acetic tartaric and citric acid do not interfere, nor do large amounts (up to 10–20%) of organic solvents, such as methanol, ethanol, ethylacetate, or chloroform, but acetone decreases the color intensity. Isopropanol and butanol completely inhibit the reactions. Aliphatic amines (diethylamine), aminoalcohols (triethanolamine), aminoacids (cycline) and chelating agents (EDTA) do not interfere.

The reagents are suitable for the determination of the nitrate content of natural waters such as drinking water, river and saline waters, since an amount of up to 2000 ppm (mg/liter) chloride ion does not interfere, and high chloride content, as in sea water, has only a slight effect on the color development and stability. Most of the metal ions do not interfere in the color reaction, but a pre-treatment with cation exchange resin is recommended for sewage samples. The reagent can also be used for soil and plant extracts, biological fluids, etc. For the detection of nitrate ion the spot test technique can be used. One drop of sample solution mixed with several drops of reagent solution develops a blue or a violet color in a few seconds or minutes.

The new reagents of the present invention are characterized by very high selectivity and sensitivity. As little as 0.1 mg/liter nitrate ion can be detected with certainty by the appearance of blue color, or at least 1 mg/liter nitrate by the appearance of violet color, when aqueous sample solutions are mixed with one of the colorless reagent solutions. Less than 0.005 g $NO^-$ can be easily detected by use of the spot test technique or when a solid reagent in powder or tablet form is used in combination with concentrated sulfuric acid.

The new reagents according to the present invention possess considerable advantages in comparison with previously known detection and determination reactions for nitrate ions. For the first time it is possible to detect specifically micro amounts of nitrates in a rapid and simple way and it is possible to perform quickly precise quantitative determinations with very sensitive and specific nitrate reagents. The reagents are stable, and are neither toxic nor carcinogenic. They are colorless and no decolorization occurs over several months even if they are exposed to the influence of diffused daylight.

While the invention will now be described in connection with certain preferred embodiments in the following illustrative examples it will be understood that it is not intended to limit the invention to these particular embodiments. On the contrary it is intended to cover all alternatives, modifications and equivalents as may be included within the scope of the invention as defined by the appended claims. Thus, the following examples which include a preferred embodiment will serve to illustrate the practice of this invention, it being understood that the particulars shown are by way of example and for purposes of illustrative discussion of preferred embodiments of the present invention only and are presented in the cause of providing what is believed to be the most useful are readily understood description of procedures as well as of the principles and conceptual aspects of the invention.

EXAMPLE 1

Reagent contains:
0.050 g diphenylamine
1 g 4,4'-sulfonyldianiline
1 g ammonium chloride
in 1 liter of a mixture of equal volumes of sulfuric acid 96–98% and phosphoric acid 84–85%.

Determination procedure 1 ml aqueous nitrate sample is mixed with 5 ml reagent. After 10–30 minutes the developed blue color intensity is read at 600 nm in 1 cm cell, or compared with color standards. Range 1–10 ppm $NO_3^-$.

EXAMPLE 2

Reagent contains:
0.020 g diphenylamine
1 g 4,4'-sulfonyldianiline 0.5 g Ammonium chloride
in 1 liter of a mixture of equal volumes of sulfuric acid 96–98% and phosphoric acid 84–85%.

Determination procedure 1 ml aqueous nitrate sample is mixed with 5 ml reagent. After 10–30 minutes the developed blue color intensity is read at 600 nm in 1 cm cell, or compared with color standards. Range 0.5 – 5 ppm $NO_3^-$.

EXAMPLE 3

Reagent contains:
0.040 g 4-diphenylamine-4-sulfonic acid
1.2 g 4,4'-sulfonyldianiline
1 g hydroxylamine hydrochloride
in 1 liter of a mixture of equal volumes of sulfuric acid 96–98% and phosphoric acid 84–85%.

Determination procedure 0.05 ml aqueous nitrate sample is mixed with 5 ml reagent. The developed violet color intensity is read at 570 nm in 1 cm cell after 30–300 minutes or compared with color standards. Range 20–200 ppm $NO_3^-$.

EXAMPLE 4

Reagent contains:
0.040 g 4-diphenylamine-4-sulfonic acid sodium salt
1.2 g 4,4'-sulfonyldianiline
1 g hydroxylamine hydrochloride
in 1 liter of a mixture of equal volumes of sulfuric acid 96–98% and phosphoric acid 84–85%.

METHOD AND REAGENTS FOR THE DETECTION, ESTIMATION AND QUANTITATIVE DETERMINATION OF NITRATE IONS

The present invention is concerned with a method and reagents for the detection, estimation and colorimetric determination of nitrate ions.

Detection reactions, which are very important in analytical chemistry, are those with which specific ions can be detected specifically. Reagents which react specifically, quickly and in a simple manner can be used for semi-quantitative and/or precise determination, if the reaction product can be measured or estimated visually.

Numerous analytical methods and procedures exist for the detection and for the quantitative determination of nitrate ions. Most of these are not specific or else the procedures for precise quantitative determination are complicated and time-consuming. Many of the reagents have only very limited stability, while others are toxic.

The simplest methods for the detection and direct determination are based on reagents which give color reactions, specific for nitrate ions.

Diphenylamine and diphenylamine sulfonic acid are known as very sensitive redox indicators and they are used for the detection of nitrate ions.

Attempts were made by several researchers to prepare reagent solutions with these indicators for the quantitative determination of nitrate ions, but the resulting reagents were not suitable for precise determinations, nor were they specific for nitrate ions.

A solution containing diphenylamine and 4,4'-sulfonyldianiline was proposed as a specific reagent for the detection and determination of nitrate ions, by E. Szekely in Talanta, 1967, Vol. 14, pp. 944–50, however, the determination procedure by this method is tedious. Reliable results can be obtained only under strictly controlled conditions, e.g., use of ice-water bath, temperature control during the slow color development, etc.

According to the present invention there has now been developed a new reagent with particular constitution for rapid and simple determination of nitrate ions.

According to the present invention reagents are obtained which ensure the rapid detection, estimation and quantitative determination of nitrate ions. The reagents are stable. A blue or violet color appears after aqueous nitrate samples are mixed with the reagents. Full color develops in a few minutes and the colors remain stable for at least ½ – 1 hour. The color reactions are specific for the nitrate ions. The intensity of the colors is proportional to the nitrate content of the samples, and precise results are obtained by photometric measurements. Estimation (semiquantitative determinations) can be carried out visually by comparison with color standards.

Thus, according to the present invention there is now provided a reagent for the detection, estimation and quantitative determination of nitrate ions comprising:
a. about 0.005 to 0.05 wt/v%. of a diphenylamine redox indicator;
b. about 0.1 to 2.0 wt/v%. of a chloride selected from the group consisting of ammonium chloride, hydroxylamine hydrochloride or a mixture thereof;
c. about 0.1 to 2.0 wt/v%. 4,4'-sulfonyldianiline;
d. concentrated sulfuric acid; and
e. concentrated phosphoric acid or an alkaline dihydrogen phosphate.

Weight % figures as given herein are calculated throughout based on the total weight of all of the solid components (a)–(c) in the finally prepared reagent in volumes of the liquid components (d)–(e). Only with this special combination of the individual components can the special advantages of the new reagents be realized.

The present invention also provides a method for the detection, estimation and quantitative determination of nitrate ions comprising preparing a nitrate reagent comprising:
a. about 0.005 to 0.05 wt/v %. of a diphenylamine redox indicator;
b. about 0.1 to 2.0 wt/v %. 4,4'-sulfonyldianiline;
c. about 0.1 to 2.0 wt/v %. of a chloride selected from the group consisting of ammonium chloride, hydroxylamine hydrochloride or a mixture thereof;
d. concentrated sulfuric acid; and
e. concentrated phosphoric acid or an alkaline dihydrogen phosphate;

and combining said reagent with an aqueous nitrate sample.

The term diphenylamine redox indicator as used herein is directed to diphenylamine and those compounds containing the diphenylamine configuration which are known to be useful as redox indicators. Especially preferred are diphenylamine redox indicators selected from the group consisting of diphenylamine, diphenylbenzidine, diphenylamine sulfonic acid, diphenylbenzidine sulfonic acid and alkali or alkaline earth salts thereof.

One of the most important features of a reagent is its stability and shelf-life, and according to the present invention it has now been found that components (a), (b) and (c) or components (a), (b), (c) and (e) when component (e) is an alkaline dihydrogen phosphate can be prepared together in dry powder or tablet form and stored or shipped as such until required for use at which time said dry form can be solubilized with components (d) and (e) or (d) alone respectively to produce a liquid reagent which itself has a relatively long and stable shelf-life. Thus the present invention also provides a reagent for the detection, estimation and quantitative determination of nitrate ions upon combination with concentrated sulfuric acid and concentrated phosphoric acid or an alkaline dihydrogen phosphate comprising:
a. about 0.005 to 0.05 wt/v %. of a diphenylamine redox indicator;
b. about 0.1 to 2 wt/v %. of 4,4'-sulfonyldianiline, and
c. about 0.1 to 2.0 wt/v %. of a chloride selected from the group consisting of ammonium chloride, hydroxylamine hydrochloride or a mixture thereof;

and a reagent for the detection, estimation and quantitative determination of nitrate ions upon combination with concentrated sulfuric acid comprising:
a. about 0.005 to 0.05 wt/v %. of a diphenylamine redox indicator;
b. about 0.1 to 2 wt/v %. of 4,4'-sulfonyldianiline;
c. about 0.1 to 2.0 wt/v %. of a chloride selected from the group consisting of ammonium chloride, hydroxylamine hydrochloride or a mixture thereof, and
d. an alkaline dihydrogen phosphate.

DETERMINATION PROCESS 0.5 ml aqueous nitrate sample is mixed with 5 ml reagent. The developed violet color intensity is read at 570 nm in 1 cm cell after 10–60 minutes or compared with color standards. Range 2–20 ppm $NO_3^-$.

EXAMPLE 5

Reagent contains
0.040 g 4-diphenylamine-4-sulfonic acid barium salt
1.2 g 4,4'-sulfonyldianiline
1 g hydroxylamine hydrochloride
in 1 liter of a mixture of equal volumes of sulfuric acid 96–98% and phosphoric acid 84–85%.

Determination procedure 0.5 ml aqueous nitrate sample is mixed with 5 ml reagent. The developed violet color intensity is read at 570 nm in 1 cm cell after 10–60 minutes or compared with color standards. Range 2–20 ppm $NO_3^-$.

EXAMPLE 6

Reagent contains:
0.050 g 4-diphenylamine-4-sulfonic acid sodium salt
2 g 4,4'-sulfonyldianiline
1 g hydroxylamine hydrochloride
in 1 liter of a mixture of equal volumes of sulfuric acid 96–98% and phosphoric acid 84–85%.

Determination procedure 0.5 ml aqueous nitrate sample is mixed with 5 ml reagent. The developed violet color is read at 570 nm in 1 cm cell after 5–60 minutes, or compared with color standards. Range 5–40 ppm $NO_3^-$.

EXAMPLE 7

Reagent contains:
0.025 g diphenylbenzidine
2 g 4,4'sulfonyldianiline
0.8 g ammonium hydrochloride
in 1 liter of a mixture of 6 volumes of sulfuric acid 96–98% and 4 volumes of phosphoric acid 84–85%.

Determination procedure 1 ml aqueous nitrate sample is mixed with 5 ml reagent. The developed blue color intensity is read at 600 nm in 1 cm cell after 30–60 minutes, or compared with color standards. Range 0.1–1 ppm $NO_3^-$.

EXAMPLE 8

Reagent contains as given in Example 2.

Detection procedure 1 drop (0.04–0.05 ml) nitrate sample is mixed with 8–10 drops reagent. A blue color developed in 10 minutes indicates the presence of minimum 0.03 μg $NO_3^-$. A blue color developed in a few seconds indicates the presence of minimum 1 μg $NO_3^-$.

EXAMPLE 9

Reagent contains as given in Example 6.

Detection procedure 1 drop nitrate sample mixed with 15–20 drops reagent. A violet color developed in a few minutes indicates the presence of minimum 0.1 μg $NO_3^-$. A violet color developed in a few seconds indicates the presence of minimum 2 μg $NO_3^-$.

EXAMPLE 10

Reagent contains as given in Example 7.

Detection procedure 1 drop (0.04–0.05 ml) nitrate sample is mixed with 5–6 drops reagent. A blue color developed in about 15 minutes indicates the presence of minimum 0.005 μg $NO_3^-$. A blue color developed in a few seconds indicates the presence of minimum 0.02 μg $NO_3^-$.

EXAMPLE 11

Reagent contains:
0.040 g 4-diphenylamine-4-sulfonic acid sodium salt
1.2 g 4,4'-sulfonyldianiline
1 g ammonium chloride
500 g potassium dihydrogen phosphate

Estimation (semiquantitative determination) procedure 1 drop (0.05 ml) aqueous nitrate sample is mixed thoroughly with 0.25 g reagent (in powder or tablet form), then 0.25 ml concentrated sulfuric acid is added and mixed. The developed violet color intensity is compared after 5 minutes with color standards corresponding to a range of 2–20 ppm $NO_3^-$.

It will be evident to those skilled in the art that the invention is not limited to the details of the foregoing illustrative embodiments and that the present invention may be embodied in other specific forms without departing from the spirit or essential attributes thereof. It is therefore desired that the present embodiments be considered in all respects as illustrative and not restrictive, reference being made to the appended claims, rather than to the foregoing description in which it is intended to claim all modifications coming within the scope and spirit of the invention.

What is claimed is:

1. A method for the detection, estimation and quantitative determination of nitrate ions comprising preparing a nitrate reagent comprising:
    a. about 0.005 to 0.05 wt/v %. of a diphenylamine redox indicator;
    b. about 0.1 to 2.0 wt/v %. 4,4'-sulfonyldianiline;
    c. about 0.1 to 2.0 wt/v %. of a chloride selected from the group consisting of ammonium chloride, hydroxylamine hydrochloride or a mixture thereof;
    d. concentrated sulfuric acid; and
    e. concentrated phosphoric acid or an alkaline dihydrogen phosphate;
and combining said reagent with an aqueous nitrate sample.

2. The method of claim 1 wherein said diphenylamine redox indicator is selected from the group consisting of diphenylamine, diphenylbenzidine, diphenylamine sulfonic acid, diphenylbenzidine sulfonic acid and alkali or alkaline earth salts thereof.

3. A method according to claim 1 wherein in the determination procedure 1 volume of nitrate sample is mixed with at least 5 volumes of reagent.

4. A method according to claim 1 wherein in the determination procedure 1 volume of nitrate sample is mixed with at least 10 volumes of reagent.

5. A method according to claim 1 wherein the detection is performed by the spot test technique.

6. A method according to claim 1 wherein estimations and semiquantitative determinations are performed visually by comparison with color standards.

7. A method according to claim 1 wherein determinations are performed instrumentally.

8. A method according to claim 1 wherein quantitative determinations are performed by reading at 600 nm.

9. A method according to claim 1 wherein quantitative determinations are performed by reading at 570 nm.

10. A method according to claim 1 wherein the reagent constituents (a), (b) and (c) are prepared together in dry form and later combined with constituents (d), (e) for solubilization.

11. A method according to claim 1 wherein reagent constituent (e) is an alkaline dihydrogen phosphate and reagent constituents (a), (b), (c) and (e) are prepared together in dry form and constituent (d) is added during the estimation procedure.

12. A reagent for the detection, estimation and quantitative determination of nitrate ions upon combination with concentrated sulfuric acid and concentrated phosphoric acid or an alkaline dihydrogen phosphate comprising
 a. about 0.005 to 0.05 wt/v %. of a diphenylamine redox indicator;
 b. about 0.1 to 2 wt/v %. of 4,4'-sulfonyldianiline, and
 c. about 0.1 to 2.0 wt/v %. of a chloride selected from the group consisting of ammonium chloride, hydroxylamine hydrochloride or a mixture thereof.

13. A reagent for the detection and estimation of nitrate ions upon combination with concentrated sulfuric acid comprising:
 a. about 0.005 to 0.05 wt/v %. of a diphenylamine redox indicator;
 b. about 0.1 to 2 wt/v %. of 4,4'-sulfonyldianiline;
 c. about 0.1 to 2.0 wt/v %. of a chloride selected from the group consisting of ammonium chloride, hydroxylamine hydrochloride or a mixture thereof; and
 d. an alkaline dihydrogen phosphate.

14. A reagent for the detection, estimation and quantitative determination of nitrate ions comprising:
 a. about 0.005 to 0.05 wt/v %. of a diphenylamine redox indicator;
 b. about 0.1 to 2.0 wt/v %. 4,4'-sulfonyldianiline;
 c. about 0.1 to 2.0 wt/v %. of a chloride selected from the group consisting of ammonium chloride, hydroxylamine hydrochloride or a mixture thereof.
 d. concentrated sulfuric acid; and
 e. concentrated phosphoric acid or an alkaline dihydrogen phosphate.

15. A reagent according to claim 14 wherein said diphenylamine redox indicator is selected from the group consisting of diphenylamine, diphenylbenzidine, diphenylamine sulfonic acid, diphenyl benzidine sulfonic acid and alkali or alkaline earth salts thereof.

16. A reagent according to claim 14 wherein said indicator is diphenylamine.

17. A reagent according to claim 14 wherein said indicator is 4-diphenylamino-4-sulfonic acid.

18. A reagent according to claim 14 wherein said indicator is 4-diphenylamine-4-sulfonic acid sodium salt.

19. A reagent according to claim 14 wherein said indicator is 4-diphenylamine-4-sulfonic acid barium salt.

20. A reagent according to claim 14 wherein said indicator is diphenyl benzidine.

21. A reagent according to claim 14 wherein the chloride is ammonium chloride.

22. A reagent according to claim 14 wherein the chloride is hydroxylamine hydrochloride.

23. A reagent according to claim 14 wherein component e is concentrated phosphoric acid.

24. A reagent according to claim 14 wherein component e is an alkaline dihydrogen phosphate.

* * * * *